United States Patent
Mueller-Rees et al.

(10) Patent No.: US 8,586,344 B2
(45) Date of Patent: Nov. 19, 2013

(54) TUBULAR PHOTOBIOREACTOR

(75) Inventors: Christoph Mueller-Rees, Pullach (DE);
Rupert Pfaller, Munich (DE); Christian Walter, Burghausen (DE); Fritz Cotta, Merseburg (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/501,899

(22) PCT Filed: Oct. 19, 2010

(86) PCT No.: PCT/EP2010/065739
§ 371 (c)(1),
(2), (4) Date: Apr. 13, 2012

(87) PCT Pub. No.: WO2011/048108
PCT Pub. Date: Apr. 28, 2011

(65) Prior Publication Data
US 2012/0202290 A1  Aug. 9, 2012

(30) Foreign Application Priority Data
Oct. 20, 2009  (DE) .......................... 10 2009 045 851

(51) Int. Cl.
*C12N 1/12*  (2006.01)

(52) U.S. Cl.
USPC .................. 435/257.3; 435/257.6; 435/292.1; 435/410; 47/1.4

(58) Field of Classification Search
USPC ............. 435/292.1, 252.1, 257.3, 257.6, 410; 47/1.4
See application file for complete search history.

(56) References Cited

U.S. PATENT DOCUMENTS

| 5,958,761 | A | 9/1999 | Yogev et al. |
| 2004/0210024 | A1 | 10/2004 | Schafer et al. |
| 2004/0254325 | A1 | 12/2004 | Kuepfer et al. |
| 2009/0143496 | A1 | 6/2009 | Ziche |
| 2009/0205638 | A1* | 8/2009 | Corcoran ...................... 126/683 |
| 2010/0190227 | A1 | 7/2010 | Dauth et al. |

FOREIGN PATENT DOCUMENTS

| DE | 29707043 U1 | 1/1998 |
| EP | 0239272 B1 | 9/1987 |
| EP | 1412416 B1 | 4/2004 |
| EP | 1489129 B1 | 12/2004 |
| GB | 2205581 A | 12/1988 |
| JP | 09121835 A | 5/1997 |

(Continued)

OTHER PUBLICATIONS

Chen Si-ye, Q I Han-shi. "Photolithotrophic cultivation of Laminaria japonica Gametohyte Cells in Strirred Tank Photobioreactors: stuides in Different Pulse Feeding Modes". China Biotechnology. vol. 28, Issue 1, pp. 36-43. 2008.*

(Continued)

*Primary Examiner* — Michael Hobbs
(74) *Attorney, Agent, or Firm* — Caesar, Rivise, Bernstein, Cohen & Pokotilow, Ltd.

(57) ABSTRACT

The invention relates to a tubular photobioreactor that has a core structure in the shape of a truncated cone and one or more transparent or translucent tubes which are helically wound around the outer surface and/or inner surface of the core structure. The tubular photobioreactor is characterized in that the transparent or translucent tube has at least two chambers, through at least one of which the cultivation medium flows and through at least one of which a heat transfer medium flows.

16 Claims, 3 Drawing Sheets

(56) References Cited

FOREIGN PATENT DOCUMENTS

| WO | 9928018 A1 | 6/1999 |
|---|---|---|
| WO | 2006058656 A2 | 6/2006 |
| WO | 2007129327 A1 | 11/2007 |
| WO | 2008097845 A1 | 8/2008 |
| WO | 2008145719 A1 | 12/2008 |

OTHER PUBLICATIONS

International Search Report for PCT/EP2010/065739 dated May 6, 2011.
G Hillesheim, Doppelt Hält Besser—Vom Doppelmantel-System zum Wärmeträgerschlauch—Chemietechnik_de 2008, http://www.chemietechnik.de/texte/anzeigen/105682, searched Oct. 7, 2010.
English Abstract corresponding to G Hillesheim, Doppelt Hält Besser—Vom Doppelmantel-System zum Wärmeträgerschlauch—Chemietechnik_de 2008, http://www.chemietechnik.de/texte/anzeigen/105682, searched Oct. 7, 2010.
"Ein Schlauch im Schlauch", innovations-report Jun. 1, 2006, http://www.innovation-report.de/berichte/maschinenbau/schlauch_schlauch_134975.html, searched Oct. 7, 2010.
English Abstract corresponding to "Ein Schlauch im Schlauch", innovations-report Jun. 1, 2006, http://www.innovationreport.de/berichte/maschinenbau/schlauch_schlauch_134975.html, searched Oct. 7, 2010.
English Abstract corresponding to JP 09-121835 A.
Winnacker/Küchler, Chemische Technik: Prozesse und Produkte, vol. 5: "Organische Zwischenverbindungen, Polymere", p. 1095-1213, Wiley-VHC Weinheim (2005).
English Abstract corresponding to Winnacker/Küchler, Chemische Technik: Prozesse und Produkte, vol. 5: "Organische Zwischenverbindungen, Polymere", p. 1095-1213, Wiley-VHC Weinheim (2005).

* cited by examiner

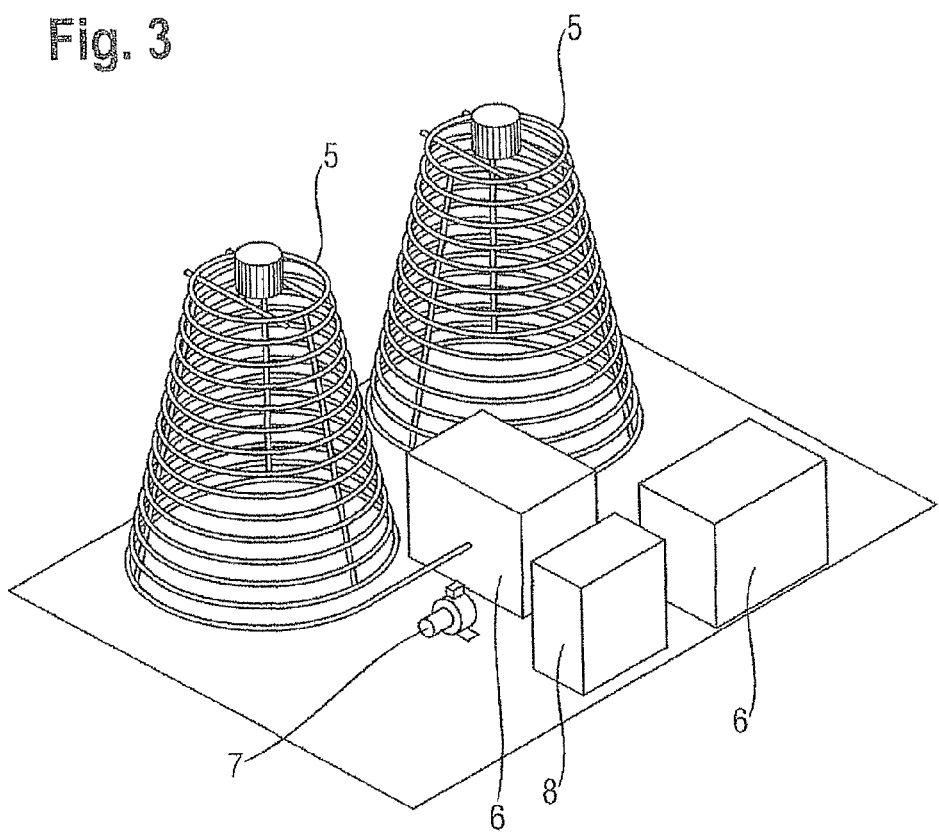

TUBULAR PHOTOBIOREACTOR

BACKGROUND OF THE INVENTION

The invention relates to a tubular photobioreactor and to the culturing of phototrophic macro- or microorganisms using a photobioreactor such as this.

Photobioreactors are used for the large-scale production of phototrophic organisms, e.g. cyanobacteria or microalgae, for example *Spirulina, Chlorella, Chlamydomonas* or *Haematococcus*. Microalgae of this type are able to convert light energy, $CO_2$ and water into biomass. Photobioreactors of the first generation use sunlight as the light source. The reactors consist of large open tank units of a variety of designs, for example round tank units with diameters up to 45 m and rotating mixing arms. These reactors are generally made of concrete or plastics. Closed bioreactors are also used in various forms. Closed bioreactors can be plate bioreactors, tube bioreactors, (bubble) column bioreactors or tubular bioreactors. This type of reactor is made of transparent or translucent materials, such as glass or plastic.

Closed photobioreactors offer the advantage that the production of biomass can take place under controlled conditions and contamination of the culture can be suppressed. To improve the light input into the cultures by increasing the surface/volume ratio, tube or tubular photobioreactors are recommended, wherein to reduce the space requirement the tubes or tubing are wound helically round a cylindrical framework.

WO 2007/129327 A1 describes a photobioreactor that contains at least two transparent, spiral tubes, each wound round a cylindrical supporting framework, wherein the individual tube elements are joined together by their free ends. The tubes are preferably made of silicones. The reactor is illuminated by means of tubular lighting elements, which are arranged in the annular gaps between the individual spiral tube elements. Temperature control of the tube system is provided by a heat exchanger arranged outside of the helical arrangement. There is the problem here that the temperature conditions are non-uniform owing to the externally arranged heat exchanger and the different radiation intensity in the upper and lower portions of the reactor with the cylindrical-helical geometry. EP 239272 B1 describes a photobioreactor with a vertical core structure, which can be cylindrical or in the form of a cone. A transparent tube is wound helically round the outside of the core structure. Polyethylene is recommended as tube material. A heat exchanger arranged outside of the helical structure is recommended for temperature control. Illumination takes place externally by insolation. To increase the light intensity it is recommended to provide the inside of the core structure with a reflective coating or install artificial light sources in the core structure. This design has the drawbacks of variable radiation intensity with the cylindrical core structure, and inadequate temperature control with the external heat exchanger.

GB 2205581 A describes a photobioreactor with a cylindrical core structure or a core structure in the form of a truncated cone. One or two transparent plastic hoses are wound helically round the outside of this core structure. As an alternative, it is also possible for one hose to be arranged helically on the inside and one on the outside of the core structure. Transparent plastic or glass is recommended as hose material. Illumination is by sunlight or artificial light sources, which are fitted between the inside and outside of the core structure. No devices for attemperation of the culture medium are described. WO 2008/097845 A1 describes a photobioreactor with a cylindrical core structure, wherein helically wound hoses made of transparent plastic are arranged round the core structure. Temperature control is provided by a heat exchanger mounted on the inside of the core structure. DE 29707043 U1 describes a photobioreactor with a transparent, tubular pipeline, filled with culture medium, encircling a carrying frame. To increase light supply, a light source is arranged inside the carrying frame, and a converging lens on the upper end of the carrying frame. To cool the circulating culture medium, it is recommended to provide air slots in the base of the carrying frame, for climate control of the internal space. U.S. Pat. No. 5,958,761 describes a cylindrical bioreactor for cultivation of algae, which is made of glass and comprises an outer cylinder with larger diameter, and an inner glass cylinder with smaller diameter. The inner cylinder is filled with the algal culture and is equipped with an agitator. To improve the light input, the outer cylinder is filled with a liquid whose refractive index is appropriate to the geometric ratio of inner and outer cylinders. This liquid can also serve as coolant. For further improvement of the light input it is recommended to place the glass cylinder in a mirrored parabolic trough. This has the drawback of unfavorable flow conditions in the inner cylinder, necessitating the installation of a complicated stirring unit.

Against this background, the problem was to provide a photobioreactor that is characterized, relative to the aforementioned prior art, in that the light input and temperature control are as uniform as possible throughout the reactor volume.

SUMMARY OF THE INVENTION

The invention relates to a tubular photobioreactor with a core structure of truncated cone shape and one or more transparent or translucent hoses, which are wound helically round the outside and/or inside of the core structure, characterized in that the transparent or translucent hose has at least two chambers, with the culture medium flowing through at least one of them and a heat-transfer medium flowing through at least one of them.

BRIEF DESCRIPTION OF THE DRAWINGS

FIG. 3 shows a perspective view of a two-photobioreactor embodiment of the invention.

DETAILED DESCRIPTION OF THE INVENTION

The tubular photobioreactor is suitable for cultivating phototrophic macro- or microorganisms in aqueous medium. Phototrophic organisms are defined as those that require light and carbon dioxide, or optionally a further carbon source, for growth. Examples of phototrophic macroorganisms are macroalgae, plants, mosses, plant cell cultures. Examples of phototrophic microorganisms are phototrophic bacteria such as purple bacteria and phototrophic microalgae including cyanobacteria. The tubular photobioreactor is preferably used for the cultivation of phototrophic microorganisms, especially preferably for the cultivation of phototrophic microalgae. Suitable culture media contain, as well as water and macro- or microorganisms, preferably also nutrient salts and/or substances that promote growth or product formation, optionally organic or inorganic carbon sources, for example bicarbonates or sodium hydrogen carbonate. The culture medium can optionally in addition be buffered with respect to the pH.

Water is preferably used as the heat-transfer medium.

Figure 1:
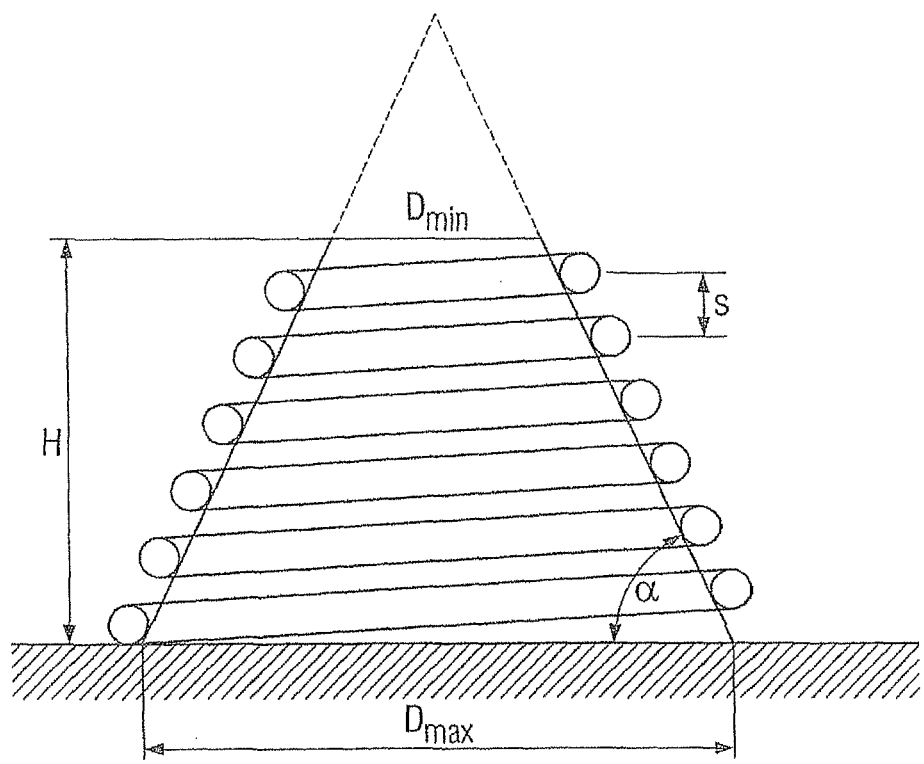
FIG. 1 shows a schematic cross-sectional view of an embodiment of a tubular photobioreactor of the invention.

The basic construction of the tubular photobioreactor is illustrated in FIG. 1. The core structure is in the shape of a truncated cone with a diameter Dmax at the base, a diameter Dmin at the top with height H, and a tilt angle α. Core structures of truncated cone shape are to be understood as three-dimensional structures with a rounded or polygonal base and with sides sloping inwards at a tilt angle α. In the case of a rounded base, this can be circular or oval. Polygonal bases comprise any polygons such as quadrangle or octagon. The core structure can also deviate from an ideal frustum, so that the sides slope inwards increasingly with increasing height, resulting in an "igloo-like" core structure or a "kinked truncated cone". All the aforementioned embodiments are to be included under the designation "core structure of truncated cone shape".

The core structure can have a continuous surface and can for example be constructed from plates. Examples are (light) metal plates such as a steel or aluminum plate, or also plastic plates, preferably transparent plastic plates, for example polyvinyl chloride or polycarbonate plates, or wooden plates.

The core structure can also have a perforated surface. Any materials, such as wood, plastics or metal, can be used for the supporting structure. For example, it can be constructed from a metal or plastic trellis. The core structure is preferably constructed from metal supports, optionally with corresponding metal crossties. The metal is preferably steel or light metals such as aluminum.

For dimensioning the core structure of truncated cone shape, several factors have to be taken into account. The tilt angle α is to be designed for optimum light harvesting. A fixed angle can be selected, optimized with respect to the place of installation and total annual light yield. The core structure of truncated cone shape can also be constructed in such a way that the tilt angle α can be varied, for example by means of telescopic poles as metal supports. In the case of kinked truncated cones, the tilt angle α in the upper region of the truncated cone can be selected to be smaller than at the base. The larger the tilt angle α, the smaller the area required for the tubular photobioreactor. However, with increasing tilt angle α there is also an increase in shadowing. At Central European latitudes, the optimum overall annual tilt angle for utilization of solar energy, according to data for solar panels, is about 30° to 50°. The tilt angle α is therefore generally from 20° to <90°, preferably 20° to 70°, especially preferably 30° to 50°.

Dmax and Dmin can in principle be selected arbitrarily. For industrial use the diameter Dmax is generally 0.9 m to 5 m, preferably 2 m to 3.5 m. In industrial use the Dmax/Dmin ratio is generally from 2 to 5, preferably from 2.5 to 4. The height of the core structure of truncated cone shape is generally 0.5 m to 5 m, preferably 0.5 m to 3 m.

The transparent or translucent hose is wound helically. Preferably the hose is wound only on the outside of the core structure of truncated cone shape. The hose is preferably wound with an increasing angle round the core structure, with the angle of inclination depending on the dimensioning of the core structure. The hose winding can consist of just one continuous hose. Several hose modules can also be joined together to form a continuous hose. The hose winding can also be composed of several hoses that are not joined together. A hose winding that is made up of several hoses has the advantage that removal of the oxygen formed during cultivation is facilitated.

The distance S, i.e. the distance between the centers of the cross section of two superposed hose segments, as a measure for the distance between the windings is ≥2r, where r is the radius of the hose cross section. To improve the light input into the hoses, the windings can also be spaced apart. Therefore the distance S is preferably 2r≤S≤4r.

Figure 2:
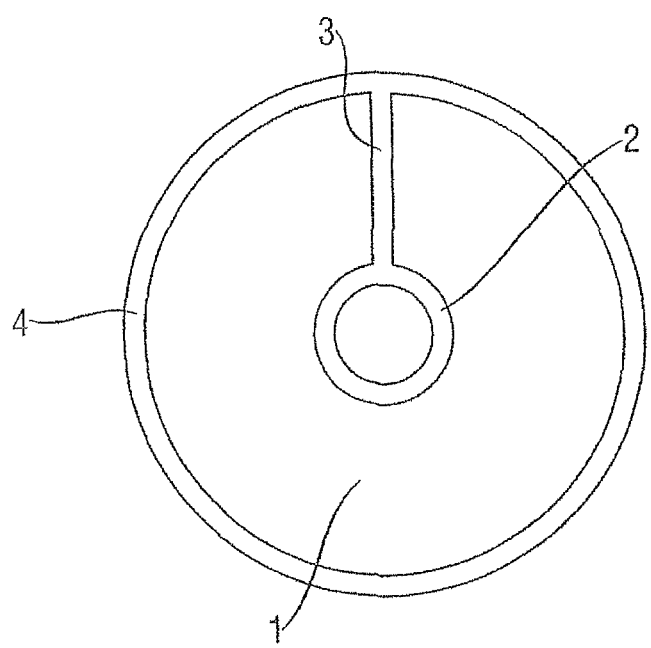
FIG. 2 shows a cross-sectional view of an embodiment of a hose of the invention.

The transparent hose comprises two or more chambers, with the culture medium flowing through at least one of them and a heat-transfer medium flowing through at least one of them. The hose can have a polygonal or rounded cross section. Preferably the hose has a circular or oval cross section. The hose can be divided into two or more chambers, for example by installing webs. For example, hoses can be used that are divided into two chambers by means of a radially arranged web. It is also possible to use hoses that contain one or more inner hoses, which can optionally be connected in each case via a web to the outer hose. However, a procedure can also be followed such that one or more hoses with smaller diameter are inserted in an outer hose of larger diameter. A hose that is made up of an outer hose and a coaxially arranged inner hose is preferred. A hose 1 (double hose), which contains a coaxially arranged inner hose 2 that is connected via a web 3 to the outer hose 4, is especially preferred; such as the double hose shown in FIG. 2, where the dimensions are only shown in principle.

The dimensioning of the hoses depends on the dimensioning of the core structure of truncated cone shape. The larger the dimensions of the core structure, the longer the hose. The diameter of the hose also depends on the dimensioning of the core structure of truncated cone shape. The smaller the diameters of the core structure, the smaller the bend radii of the hose. The diameter of the hose is therefore to be dimensioned so that it can be wound helically round the core structure of truncated cone shape without the hose kinking.

The length of the hose can be up to several hundred meters, preferably 50 m to 100 m. With lengths of the hose winding above 100 m it is preferable for the hose winding to be composed of several hoses, each preferably with a length of 50 to 100 m. The wall thicknesses of the hose or of the webs that divide the internal space of the hose into separate chambers, as well as the wall thickness of optional inner hoses, depends on the dimensioning of the hose. The wall thicknesses are generally 1 to 10 mm, preferably 2 to 5 mm. The diameter of the hose is generally not more than 200 mm, preferably 5 to 100 mm. In embodiments with one or more inner hoses, their diameters are dimensioned correspondingly smaller.

The hoses are made at least partially, preferably completely, of transparent or translucent materials. Transparent materials are to be understood as those that let through at least 80% of the light in the region of the spectrum from 400 nm to 1000 nm. Translucent materials are to be understood as those that let through at least 50% of the light in the region of the spectrum from 400 nm to 1000 nm. Transparent materials are preferred.

It is important that those regions of the hose that are arranged between the culture medium and the light source or light sources for illuminating the culture medium are made of transparent/translucent materials. If the culture medium is in the outer hose and the heat-exchange medium in an inner segment or hose, which are in each case surrounded by the culture medium, the hose containing the heat-exchange medium or the hose segment containing the heat-exchange medium can be made of nontransparent or nontranslucent materials.

Suitable materials are glass and plastics, for example homo- or copolymers such as polymethylmethacrylate (Plexiglas), polyesters such as PET, polycarbonate, polyamide, polystyrene, polyethylene, polypropylene, polyvinyl chloride or silicone materials such as silicones or copolymers with silicone and organocopolymer segments.

For the components of the hose that come into contact with the culture medium, silicone materials such as silicones or copolymers with silicone and organocopolymer segments are preferred. A procedure can also be used in which the components of the hose that come into contact with the culture medium are coated with silicone materials such as silicones or copolymers with silicone and organocopolymer segments, if they are not made of these materials.

Especially preferably, the hoses are made of transparent or translucent silicone materials.

Silicones that are preferred for production of the hoses are addition-crosslinking silicones (silicone rubbers), wherein the addition crosslinking can be initiated thermally or by radiation, and copolymers with silicone and organopolymer segments (silicone hybrid polymers).

Addition-crosslinking silicone rubber systems contain
a) organosilicon compounds having residues with aliphatic carbon-carbon multiple bonds,
b) optionally organosilicon compounds with Si-bonded hydrogen atoms or instead of a) and b)
c) organosilicon compounds having residues with aliphatic carbon-carbon multiple bonds and Si-bonded hydrogen atoms,
d) catalysts that promote the addition of Si-bonded hydrogen to aliphatic multiple bond and
e) optionally agents that delay the addition of Si-bonded hydrogen to aliphatic multiple bond at room temperature.

Solid silicone rubbers that crosslink with temperature rise (HTV) are especially preferred addition-crosslinking silicone rubbers.

Addition-crosslinked HTV silicone rubbers are obtained by the crosslinking of organopolysiloxanes multiply substituted with ethylenically unsaturated groups, preferably vinyl groups, with organopolysiloxanes multiply substituted with Si—H groups in the presence of platinum catalysts.

One of the components of the addition-crosslinking HTV-silicone rubbers preferably consists of dialkylpolysiloxanes of structure $R_3SiO[-SiR_2O]_n-SiR_3$ with n≥0, generally with 1 to 4 carbon atoms in the alkyl residue R, wherein the alkyl residues can be replaced completely or partially with aryl residues such as the phenyl residue and, at one or at both ends, one of the terminal residues R is replaced with a polymerizable group such as the vinyl group. However, polymers with side or with side and terminal vinyl groups can also be used. Vinyl-end-blocked polydimethylsiloxanes of structure $CH_2=CH_2-R_2SiO[-SiR_2O]_n-SiR_2-CH_2=CH_2$ are preferably used, as well as vinyl-end-blocked polydimethylsiloxanes of the stated structure which also bear vinyl side groups. In the case of addition-crosslinking HTV silicone rubbers, the second component is a copolymer of dialkylpolysiloxanes and polyalkylhydrogensiloxanes of general formula $R'_3SiO[-SiR_2O]_n-[SiHRO]_n-SiR'_3$ with m≥0, n≥0 and R with the meaning given above, with the proviso that at least two SiH groups must be present, wherein R' can represent H or R. Accordingly there are crosslinking agents with side and terminal SiH groups, whereas siloxanes with R'=H, which only possess terminal SiH groups, are also still used for chain extension. Platinum catalysts are used as crosslinking catalysts. HTV silicone rubbers are also processed as a single-component system.

Silicone hybrid polymers are also suitable materials. Silicone hybrid polymers are copolymers or graft copolymers of organopolymer blocks, for example polyurethane, polyurea or polyvinyl esters, and silicone blocks, generally based on polydialkylsiloxanes of the aforementioned specification. For example, thermoplastic silicone hybrid polymers are described in EP 1412416 B1 and EP 1489129 B1, the relevant disclosure of which is also to be subject matter of the present application. Silicone hybrid polymers of this kind are called thermoplastic silicone elastomers (TPSEs). Suitable materials are also (condensation- or radiation-) crosslinkable silicone hybrid materials, as described in WO 2006/058656, the relevant disclosure of which is also to be subject matter of the present application.

A detailed review of silicones, their chemistry, formulation and application properties is given for example in Winnacker/Küchler, [Chemische Technik: Prozesse and Produkte, Band 5: Organische Zwischenverbindungen, Polymere] [Chemical Engineering: Processes and Products, Vol. 5: Organic Intermediates, Polymers], pp. 1095-1213, Wiley-VCH Weinheim (2005).

The surface morphology of the silicone hoses is also essential for inhibition or prevention of fouling with microorganisms. The surface morphology is determined from the contact angle of this surface with water.

Surfaces with contact angles between 100° and 120° are preferred, surfaces with contact angles between 100° and 115° are especially preferred, and surfaces with contact angles between 100° and 113° are most especially preferred. The contact angle is adjusted through selection of the silicone materials. Other measures for increasing the contact angle, for example roughening of the surface (e.g. imitation of the so-called lotus effect), are preferably not used. Such roughening can in fact disturb the cultivation of the phototrophic microorganisms. The contact angle of the surface of the silicone hoses with water can be determined by methods known to a person skilled in the art, for example according to DIN 55660-2, using commercially available measuring instruments for determining the contact angle, for example the contact angle measuring systems obtainable from the company Krüss.

Optionally the stated addition-crosslinked silicones can contain usual additives for promoting adhesion or usual fillers or fibrous materials for improving the mechanical properties. These additives are preferably used at most in amounts such that the silicone molding remains transparent or translucent. Light-conducting additives and light-wave-shifting additives can also be added.

Preferably, silicone materials are also used for coating the components of the hose that come into contact with the culture medium, especially if the components are not made of the stated silicone materials.

Silicone materials preferred as coating agent are, in addition to the silicone materials already mentioned for production of the hoses, silicone rubbers crosslinking by condensation even at room temperature, and room-temperature addition-crosslinking silicone rubbers and silicone resins and silicone gels.

Silicone rubbers suitable as coating agents, and crosslinking at room temperature by condensation, are room-temperature-crosslinking 1-component systems, so-called RTV-1 silicone rubbers. The RTV-1 silicone rubbers are organopolysiloxanes with condensable end groups, which crosslink in the presence of catalysts by condensation at room temperature. The commonest are dialkylpolysiloxanes of structure $R_3SiO[-SiR_2O]_n-SiR_3$ with a chain length of n>2. The alkyl residues R can be identical or different and generally have 1 to 4 carbon atoms and can optionally be substituted. The alkyl residues R can also be replaced partially with other residues, preferably with aryl residues, which are optionally substituted, and wherein the alkyl (aryl) groups R are partially exchanged with condensation-crosslinkable groups, for example alcohol residues (alkoxy system), acetate residues (acetic acid system), amine residues (amine system) or oxime residues (oxime system). The crosslinking is catalyzed by suitable catalysts, for example tin or titanium catalysts.

Room-temperature condensation-crosslinking silicone rubbers suitable as coating agents are also room-temperature-crosslinking 2-component systems, so-called RTV-2 silicone rubbers. RTV-2 silicone rubbers are obtained by condensation crosslinking of organopolysiloxanes multiply substituted with hydroxyl groups in the presence of silicic acid esters. Alkylsilanes with alkoxy groups (alkoxy system), oxime groups (oxime system), amine groups (amine system) or acetate groups (acetic acid system) can also be used as crosslinking agents, which in the presence of suitable condensation catalysts, for example tin or titanium catalysts, crosslink with the hydroxyl-group-terminated polydialkylsiloxanes.

Examples of the polydialkylsiloxanes contained in RTV-1 and RTV-2 silicone rubber are those of formula $(OH)R_2SiO[-SiR_2O]_n-SiR_2(OH)$ with a chain length of n>2, wherein the alkyl residues R can be identical or different, generally contain 1 to 4 carbon atoms and optionally can be substituted. The alkyl residues R can also be replaced partially with other residues, preferably with aryl residues, which optionally are substituted. Preferably the polydialkylsiloxanes contain terminal OH groups, which crosslink at room temperature with the silicic acid esters or the alkylsilane/tin(titanium) catalyst system.

Examples of the alkylsilanes with hydrolyzable groups, contained in RTV-1 and RTV-2 silicone rubbers, are those of formula $R_aSi(OX)_{4-a}$, with a=1 to 3 (preferably 1), and X with the meaning of R" (alkoxy system), C(O)R" (acetic acid system), N=CR"$_2$ (oxime system) or NR"$_2$ (amine system), wherein R" denotes a monovalent hydrocarbon residue with 1 to 6 carbon atoms.

Silicone rubbers suitable as coating agents, and addition-crosslinking at room temperature, are room-temperature-crosslinking 1-component systems, so-called addition-crosslinking RTV-1 silicone rubbers, room-temperature-crosslinking 2-component systems, so-called addition-crosslinking RTV-2 silicone rubbers or also room-temperature-crosslinking multicomponent systems. The crosslinking reaction can be initiated cationically, by means of appropriate catalysts, or radically, by means of peroxides, or by radiation, in particular UV radiation, or thermally.

Addition-crosslinking RTV-2 silicone rubbers are obtained by crosslinking, catalyzed by Pt catalysts, of multiply ethylenically unsaturated groups, preferably vinyl groups, substituted organopolysiloxanes with organopolysiloxanes multiply substituted with Si—H groups in the presence of platinum catalysts.

Preferably one of the components consists of dialkyl polysiloxanes of structure $R_3SiO[-SiR_2O]_n-SiR_3$ with n≥0, generally with 1 to 4 carbon atoms in the alkyl residue, wherein the alkyl residues can be replaced completely or partially with aryl residues such as the phenyl residue, and at one or at both ends one of the terminal residues R is replaced with a polymerizable group such as the vinyl group. It is also possible for the residues R in the siloxane chain, also in combination with the residues R of the end groups, to be replaced partially with polymerizable groups. Vinyl-end-blocked polydimethylsiloxanes of structure $CH_2=CH_2-R_2SiO[-SiR_2O]_n-SiR_2-CH_2=CH_2$ are preferably used.

The second component contains an Si—H-functional crosslinking agent. The polyalkylhydrogensiloxanes usually employed are copolymers of dialkylpolysiloxanes and polyalkylhydrogensiloxanes with the general formula $R'_3SiO[-SiR_2O]_n-[SiHRO]_m-SiR'_3$ with m≥0, n≥0 and with the proviso that at least two SiH groups must be present, wherein R' can represent H or R. There are accordingly crosslinking agents with side and terminal SiH groups, whereas siloxanes with R'=H, which only possess terminal SiH groups, can also still be used for chain extension. Small amounts of an organoplatinum compound are also contained as crosslinking catalyst.

Moreover, special silicone rubbers have recently become commercially available, which are crosslinked by the addition reaction described, wherein special platinum complexes or platinum/inhibitor systems are activated thermally and/or photochemically and thus catalyze the crosslinking reaction.

Silicone resins are also suitable materials for production of the transparent or translucent coating. Generally the silicone resins contain units with the general formula $R_b(RO)_cSiO_{(4-b-c)/2}$, in which b is equal to 0, 1, 2 or 3, c is equal to 0, 1, 2 or 3, with the proviso that b+c≥3, and R has the meaning given for it above, which form a highly crosslinked organo-silicone network. Silicone resins can be used as solvent-free, solvent-containing or as aqueous systems. Furthermore, it is also possible to use functionalized silicone resins, e.g. silicone resins functionalized with epoxy or amine groups.

Silicone gels are also suitable materials for production of the transparent or translucent coating.

Silicone gels are produced from two castable components, which crosslink at room temperature in the presence of a catalyst. One of the components generally consists of dialkylpolysiloxanes of structure $R_3SiO[-SiR_2O]_n-SiR_3$ with n≥0, generally with 1 to 4 carbon atoms in the alkyl residue, wherein the alkyl residues can be replaced completely or partially with aryl residues such as the phenyl residue, and at one or at both ends one of the terminal residues R is replaced with a polymerizable group such as the vinyl group. It is also possible for residues R in the siloxane chain, also in combination with the residues R of the end groups, to be replaced partially with polymerizable groups. Vinyl-end-blocked polydimethylsiloxanes of structure $CH_2=CH_2-R_2SiO[-SiR_2O]_n-SiR_2-CH_2=CH_2$ are preferably used.

The second component contains an Si—H-functional crosslinking agent. The polyalkylhydrogensiloxanes usually employed are copolymers of dialkylpolysiloxanes and polyalkylhydrogensiloxanes with the general formula $R'_3SiO[-SiR_2O]_n-[SiHRO]_m-SiR'_3$ with m≥0, n≥0 and with the proviso that at least two SiH groups must be present, wherein R' can denote H or R. There are accordingly crosslinking agents with side and terminal SiH groups, whereas siloxanes with R'=H, which only possess terminal SiH groups, can still be used for chain extension. Small amounts of an organoplatinum compound are contained as crosslinking catalyst. Mixing the components initiates the crosslinking reaction, and the gel is formed. This crosslinking reaction can be accelerated by the action of heat and/or by electromagnetic radiation, preferably UV radiation.

A detailed review of silicones, their chemistry, formulation and application properties is given for example in Winnacker/Küchler, [Chemische Technik: Prozesse and Produkte, Band 5: Organische Zwischenverbindungen, Polymere] [Chemical Engineering: Processes and Products, Volume 5: Organic Intermediates, Polymers], p. 1095-1213, Wiley-VCH Weinheim (2005).

In a preferred embodiment, the hose materials can contain usual additives such as fillers or fibrous materials for improving the mechanical properties. These additives are preferably used in maximum amounts such that the hose material remains transparent or translucent. Light-conducting additives and light-wave-shifting additives can also be added.

Manufacture can be carried out with the established technologies of plastics processing that are used for the production of moldings. In particular, in the case of silicones, by extrusion or injection molding for the molding of thermoplastic silicones (thermoplastic injection molding), elastomeric silicones (elastomer injection molding) or thermosetting silicones (thermoset injection molding). Combination processes, e.g. exjection, can also be employed, however.

For coating, the silicones are applied in liquid form, either as pure substance, as solution or in aqueous emulsion. The viscosity of the liquid to be applied for coating is preferably from 10 mPas to 300 000 mPas. Application can be carried out by the usual techniques, preferably brush application, spraying, dipping, knife coating, casting. Dipping and spraying are especially preferred. However, other methods can be used for coating tubes, e.g. sponge application, spin-coating, extrusion or crosshead extrusion, and for flat surfaces it is additionally possible to use application by roll coating, roller coating or the lick-roll process.

The thickness of the coating is generally 10 nm to 1000 μm, preferably 1 μm to 100 μm. Optionally, the reactor parts to be coated can be pretreated to improve the adhesion of the silicones, for example by corona treatment. Optionally the silicones can contain usual additives for promoting adhesion or usual fillers for improving the mechanical properties. These additives are preferably used in maximum amounts such that the silicone coating remains transparent or translucent.

Illumination is generally with sunlight, which can optionally be supplemented with artificial light (artificial light sources). Illuminants containing LEDs are preferably used for artificial illumination. However, other artificial light sources are also suitable, for example fluorescent lamps, neon lamps, metal vapor lamps, inert gas lamps, halogen lamps, sulfur plasma lamps. In the case of illumination with artificial light sources, the cultivation conditions can be optimized by using light sources with defined wavelengths, defined intensity and optionally by means of pulsating light sources. Devices for artificial illumination are preferably installed inside the core structure, but can also be installed between the hose windings. It is also conceivable for the artificial light sources, for example in the form of LED chains, to be installed or incorporated in one or more chambers of the hoses of the tubular photobioreactor.

In each case at the ends of the hose, the individual chambers are connected to a central unit, closing the culture medium circuit and the heat-transfer medium circuit. This central unit can also be a hose with at least two chambers, similar to the hose that is used for the winding round the core structure. Preferably, the hose segments containing the heat-transfer medium are connected to a vertical central tube, arranged inside the core structure or outside of the core structure, which central tube closes the circuit for the heat-transfer medium. The hose segments containing the culture medium are preferably also connected to a vertical central tube, arranged inside the core structure or outside of the core structure, which central tube closes the circuit for the culture medium.

The preferred procedure is that in which, in a hose that is composed of an outer hose and a coaxially arranged inner hose, the inner hose is filled with culture medium and the outer hose is filled with heat-transfer medium.

The culture medium containing the phototrophic organisms is generally fed from a storage tank into the corresponding chambers of the hose or hoses. Feed can be mechanical, by means of a pump, with uniform or pulsed delivery. In the hose, feed of the culture medium can also take place by means of airlift, i.e. by means of air or by means of an air/$CO_2$ mixture or also nitrogen as carrier gas, which simultaneously provides supply of $CO_2$ to the culture medium. However, the supply of $CO_2$ or $CO_2$-containing gases can also be separate and pulsed, via a mixing system or at pump inlet, and can therefore serve for adjusting the pH in the culture medium.

In the case of operation with airlift, the hydrodynamic conditions are to be taken into account when dimensioning the tubular photobioreactor. In principle, airlift operation can be carried out in two different embodiments. The helically wound hoses are gassed and function as "riser" and the central tube serves as "downer". Conversely, the central tube can be gassed and the helically wound hoses serve as "downer". In both arrangements, a degassing device is to be installed at the upper end of the tubular photobioreactor for active gas exchange.

Feed of the culture medium can take place in any manner, laterally, from above or from below. Preferably, the culture medium is fed at the bottom end of the helically wound hose or of the helically wound hose segments, if several separate hoses are wound. The culture medium is fed from the hoses into the vertical central tube and, with appropriate density of the suspension of the culture medium, withdrawn in its bottom segment. The cultivated organisms are separated in a separator unit, for example by centrifugation, filtration or sedimentation.

The heat-transfer medium can be introduced at the top end or at the bottom end of the helically wound hose or the helically wound hose segments into the corresponding chambers. Delivery is preferably pneumatic, by pump, in cocurrent or in countercurrent flow to the culture medium. The circuit of the heat-transfer medium can optionally include a heat exchanger unit for regulating the temperature of the heat-transfer medium. The temperature of the heat-transfer medium depends essentially on the ambient temperature and can be adjusted correspondingly.

The operation of the tubular photobioreactor is preferably organized with automation technology. This includes the automated monitoring and adjustment of specific process parameters such as flow rates, temperature, gas exchange, liquid exchange, density or viscosity, salt content of the culture medium, optionally light in the case of artificial illumination (intensity, wavelength, light/darkness cycle, temporal adjustment/change).

Several tubular photobioreactors can also be connected together as individual modules in series or parallel. A rough sketch of this is shown in FIG. 3. Two tubular photobioreactors 5 are arranged next to one another in series and are supplied by two storage tanks 6. The culture medium is propelled by a common pump unit 7. The phototrophic organisms are separated from the culture medium in the separator unit 8.

The tubular photobioreactor according to the invention has the advantage that, owing to the core structure of truncated cone shape and the helical winding of the hose, light input is optimized and shadowing is reduced. The multichamber construction of the hose provides continuous temperature control over the whole length of the hose, which on the one hand makes possible the large-scale cultivation of microorganisms that are sensitive to temperature fluctuations, but also minimizes natural temperature fluctuations due to the time of day. An important advantage when using the aforementioned silicone materials is that wall deposits on the regions of the hose that come into contact with the culture medium are greatly reduced or any build-up of organisms can be removed much more easily than with the materials usually employed, such as glass.

The invention claimed is:

1. A tubular photobioreactor with a core structure of truncated cone shape and at least one transparent or translucent hose, which is wound helically around an outside and/or inside of the core structure, wherein: (a) the at least one transparent or translucent hose comprises an outer hose and a coaxially arranged inner hose connected by a web has at least two chambers, (b) at least one of the outer hose and the inner hose chambers is adapted to support a flow of a culture medium; (c) at least one of the outer hose and the inner hose chambers is adapted to support a flow of a heat-transfer medium, (d) windings of the hose are spaced apart from one another, (e) the tubular photobioreactor is adapted to deliver the culture medium in a pulsed manner and (f) the at least one transparent or translucent hose comprises silicone or comprises non-silicone materials coated with silicone materials.

2. The tubular photobioreactor as claimed in claim 1, wherein the core structure of truncated cone shape is a three-dimensional structure, with a rounded or polygonal base and with sides sloping inwards at a tilt angle $\alpha$.

3. The tubular photobioreactor as claimed in claim 1, wherein the at least one transparent or translucent hose is made of glass or plastic.

4. The tubular photobioreactor as claimed in claim 1, wherein the at least one transparent or translucent hose is made of silicone materials.

5. The tubular photobioreactor as claimed in claim 1, wherein the at least one transparent or translucent hose comprises non-silicone materials coated with silicone materials.

6. The tubular photobioreactor as claimed in claim 1, wherein several tubular photobioreactors are connected together as individual modules in series or parallel.

7. A method of production of phototrophic organisms with the tubular photobioreactor as claimed in claim 1, wherein (i) the outer hose is filled with the culture medium and the inner hose is filled with the heat-transfer medium; or (ii) the inner hose is filled with the culture medium and the outer hose is filled with the heat transfer medium.

8. The method of production as claimed in claim 7, wherein the at least one transparent or translucent hose comprises an outer hose and a coaxially arranged inner hose, the inner hose is filled with culture medium and the outer hose is filled with heat-transfer medium.

9. The method of production as claimed in claim 7, wherein the at least one transparent or translucent hose comprises an outer hose and a coaxially arranged inner hose, the inner hose is filled with heat-transfer medium and the outer hose is filled with culture medium, wherein optionally the hose containing the heat-transfer medium is made of nontransparent or nontranslucent materials.

10. The tubular photobioreactor as claimed in claim 2, wherein the at least one transparent or translucent hose is made of glass or plastic.

11. The tubular photobioreactor as claimed in claim 2, wherein the at least one transparent or translucent hose is made of silicone materials.

12. The tubular photobioreactor as claimed in claim 2, wherein the at least one transparent or translucent hose comprises non-silicone materials coated with silicone materials.

13. The tubular photobioreactor as claimed in claim 2, wherein several tubular photobioreactors are connected together as individual modules in series or parallel.

14. A method of production of phototrophic organisms with the tubular photobioreactor as claimed in claim 2, wherein (i) the outer hose is filled with the culture medium and the inner hose is filled with the heat-transfer medium; or (ii) the inner hose is filled with the culture medium and the outer hose is filled with the heat transfer medium.

15. The method of production as claimed in claim 14, wherein the inner hose is filled with culture medium and the outer hose is filled with heat-transfer medium.

16. The method of production as claimed in claim 14, wherein the inner hose is filled with heat-transfer medium and the outer hose is filled with culture medium, and wherein optionally the hose containing the heat-transfer medium is made of nontransparent or nontranslucent materials.

* * * * *